United States Patent [19]

Fortman

[11] Patent Number: 5,054,674
[45] Date of Patent: Oct. 8, 1991

[54] DISPOSABLE DENTAL FLOSS CASSETTE DISPENSER SYSTEM

[76] Inventor: Eugene J. Fortman, 2111 Telemark La., Rochester, Minn. 55901

[21] Appl. No.: 483,669

[22] Filed: Feb. 23, 1990

Related U.S. Application Data

[63] Continuation-in-part of Ser. No. 316,094, Feb. 27, 1989, abandoned.

[51] Int. Cl.$^5$ .................... B65H 75/32; A47B 81/02; A61C 15/04
[52] U.S. Cl. ........................................ 225/6; 225/42; 225/77; 242/137.1
[58] Field of Search .................... 225/1, 42, 51, 52, 6, 225/63, 64, 77; 242/137, 137.1, 138; 132/323, 324, 325; 248/109, 110, 111

[56] References Cited

U.S. PATENT DOCUMENTS

| | | | |
|---|---|---|---|
| D. 154,894 | 8/1949 | Bashore | D24/1 |
| D. 189,548 | 1/1961 | Gershen | D52/2 |
| D. 192,007 | 1/1962 | Gershen | D24/1 |
| D. 266,279 | 9/1982 | Strother | D28/64 |
| D. 271,431 | 11/1983 | Seelig | D28/64 |
| 1,454,429 | 5/1923 | Dresser | 242/138 |
| 1,455,673 | 5/1923 | Shalek | 242/138 |
| 1,858,134 | 5/1932 | Booth et al. | 225/6 |
| 1,966,463 | 7/1934 | Rose . | |
| 2,109,417 | 2/1938 | Elcan . | |
| 2,499,130 | 2/1950 | Chase | 242/138 |
| 2,893,405 | 7/1959 | Castelli . | |
| 2,909,277 | 10/1959 | Thiers et al. | 206/56 |
| 2,929,541 | 3/1960 | Castelli et al. | 225/51 |
| 2,967,651 | 1/1961 | Zackheim et al. | 225/80 |
| 2,977,033 | 3/1961 | Jones | 225/6 |
| 3,246,815 | 4/1966 | Aronson | 225/44 |
| 3,376,876 | 4/1968 | Wicklund . | |
| 3,747,611 | 7/1973 | Bennington . | |
| 3,789,859 | 2/1974 | Chambers . | |
| 3,804,102 | 4/1974 | Bennington . | |
| 3,881,502 | 5/1975 | Bennington . | |
| 3,966,055 | 6/1976 | Francavilla | 248/111 |
| 4,019,522 | 4/1977 | Elbreder . | |
| 4,084,692 | 4/1978 | Bilweis | 206/43 |
| 4,141,519 | 2/1979 | Tarrson et al. | 242/137.1 |
| 4,286,611 | 9/1981 | Talbot . | |
| 4,308,880 | 1/1982 | Graves . | |
| 4,646,766 | 3/1987 | Stallard . | |
| 4,657,034 | 4/1987 | Koski . | |
| 4,706,843 | 11/1987 | Thornton | 221/48 |
| 4,821,752 | 4/1989 | Widlak | 132/309 |

OTHER PUBLICATIONS

EPCO Technologies advertisement placed in an unidentified dental industry publication (copyright on or before about May 10, 1989).

Primary Examiner—Hien H. Phan
Attorney, Agent, or Firm—Merchant, Gould, Smith, Edell, Welter & Schmidt

[57] ABSTRACT

A dental floss dispenser system including a dental floss dispenser for retention on or attachment to a surface. The dental floss dispenser includes a self-contained disposable dental floss container or cassette, the container enclosing dental floss gathered for storage therein prior to being dispensed, and a support member. The support member includes a support mechanism for supporting and receiving the container. The container preferably includes a housing including a cap and a receptacle or upper and lower portions which can be joined together to form a single self-contained housing enclosing a spool of dental floss within an enclosure created thereby. A method of dispensing dental floss is also provided.

16 Claims, 4 Drawing Sheets

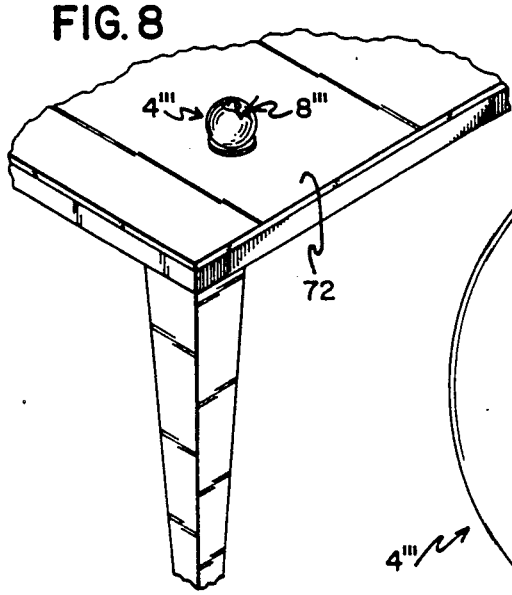
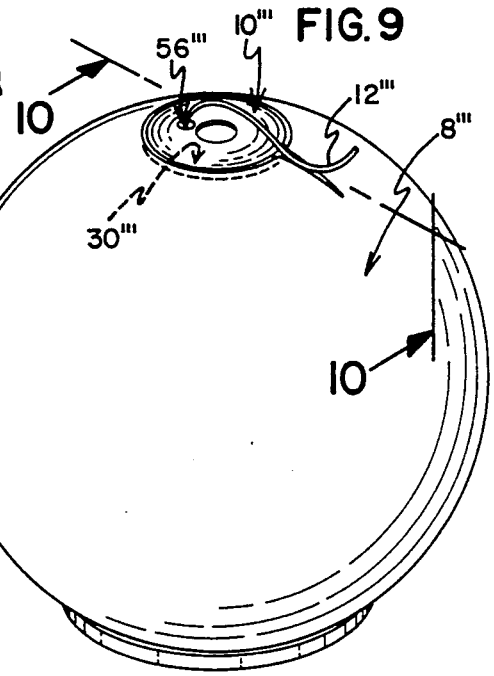
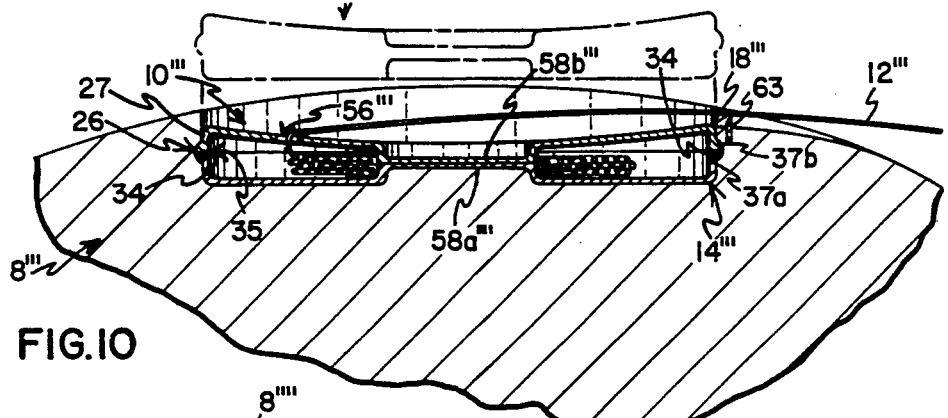
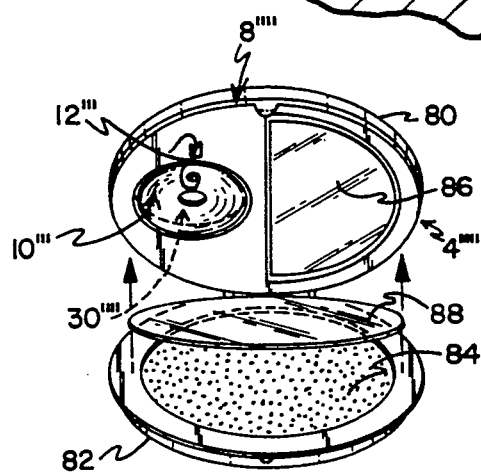
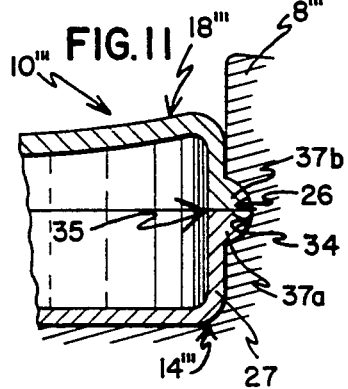

DISPOSABLE DENTAL FLOSS CASSETTE DISPENSER SYSTEM

CROSS-REFERENCE TO OTHER APPLICATIONS

The present application is a Continuation-In-Part Application of U.S. Pat. Application Ser. No. 316,094 filed Feb. 27, 1989.

FIELD OF THE INVENTION

The present invention relates to dental floss dispensers and systems for conveniently delivering clean, dry dental floss to users thereof.

BACKGROUND OF THE INVENTION

Dental floss is widely used as a means of interdental cleaning which supplements brushing. Although flossing, or the process of cleaning between one's teeth with dental floss, is becoming very common, many people find it inconvenient to use their floss regularly for lack of regular flossing habits and lack of convenient access to dental floss.

The makers of dental floss dispensers have, for this reason, tried their best to provide small containers of dental floss which may be easily stored or carried with the user. A good example is the device disclosed in U.S. Pat. No. 4,646,766 by Stallard which is easily transported in a user's pocket or stored in a medicine cabinet in one's bathroom. Somewhat larger devices, such as that disclosed by Aronson (U.S. Pat. No. 3,246,815) were disclosed earlier and are somewhat larger, but provide the same general function. It will be appreciated, however, that the convenience of a floss dispenser resulting from its small size is relative, and that no matter how conveniently sized a dispenser is, it is always easy to put away in a place where it is easily forgotten.

Other dispensers have been designed so that one's dental floss is not so easily forgotten. For example, Shalek (U.S. Pat. No. 1,455,673) discloses a dental floss dispenser which is attachable to a flat surface such as a bathroom wall, and is designed to remain in one place where it can be visible, and therefore especially convenient and present in one's mind when the user returns to that one place. In this way, the Shalek dispenser provides a convenient reminder to the user to floss his or her teeth whenever the user returns to the place where the dispenser is attached. Unfortunately, the receptacle is designed to accept an uncovered spool of floss which can result in problems related to lack of dryness or cleanliness when transferring new spools of floss into the receptacle to replenish the floss when it has run out.

Accordingly, a need exists for a dental floss dispenser system which can be attached to a wall, placed on a desk or other surface, or carried in a pocket or a purse, and can provide a renewable source of dental floss provided in a convenient manner which will assure users that the floss is clean and dry. The present invention provides a solution to this and other problems and also offers other advantages over the prior art, and solves other problems associated therewith.

SUMMARY OF THE INVENTION

Accordingly, it is an object of the present invention to provide a convenient dental floss dispenser system which may be attached to a bathroom wall where it will be available for convenient use at all times of the day. The dispenser includes a support member designed to receive a renewable dental floss cassette or floss container which is a self-contained unit which will offer users confidence that the floss contained therein is clean and dry. In order to achieve this object, the present Inventor has developed a floss dispenser for attachment to a surface. The floss dispenser comprises self-contained disposable cassette housing means for enclosing dental floss gathered for storage therein prior to being dispensed, and a support member for attachment to the surface. The support member includes support means for supporting said disposable cassette means. The support member preferably includes receiving means for receiving said disposable cassette means such that said cassette means can be easily removed and replaced. Said cassette means preferably includes a dental floss container comprising a housing. The housing provides an enclosure for substantially cleanly storage of dental floss. The housing includes introduction means for introducing dental floss into the enclosure, and a floss dispensing opening through which the floss can be passed and withdrawn over time. Preferably, the housing includes orientation means for orienting the housing with respect to the support member. In addition, the housing preferably includes a receptacle and cap means which can be joined to form the housing which is a single two-piece unit wherein the cap is joined to cover the receptacle.

It is the object of the present invention to provide a floss dispenser which can be attached to a bathroom wall, or the like, which includes a support member which supports a replaceable self-contained floss container or cassette. This will enable the user to replace the floss container with a new one when the floss in the first container is used up. The support member may be used over and over again to support any number of new containers which are preferably available for sale at one's neighborhood drugstore or dentist's office. It will be appreciated that the preferred container provides a self-contained enclosure containing a sufficient amount of floss to last for a period of time. Because the container is self-contained, the user may be ensured that the floss is clean, and has not been contaminated either during shelf storage, or during transfer from a package to the support member. Furthermore, because the container can be frequently replaced, one needn't be uneasy about the buildup of dust or the like on top of the container. If it appears that the container is dirty, it may be easily replaced.

The cassette system ensures cleanliness by keeping the floss away from contamination carried in the air or in fluids which may come into contact with floss containers. Furthermore, the floss is not exposed to the touch of one's hands prior to use. Because of the very small floss dispensing openings of the most preferred embodiments, very little air, and virtually no fluids pass into the floss container enclosure during normal use. Therefore, the floss is protected from airborne contaminants such as viral and bacterial particles or aerosols, hair spray, perfumes or other airborne contaminants which can come into contact with the floss through the air. Also, because one can insert the floss container into the support member without handling the floss, the disease chain, which might otherwise link the person inserting the floss into the floss dispenser with the user of the floss, is broken because the person who inserts the floss container in the support member does not actually handle the floss because it is enclosed within in the self-contained floss container. The container is also reasonably water tight thereby providing some assurance that disease carrying moisture will not seep into the container and contaminate the floss contained therein.

It is another object of the present invention to provide a floss dispenser which may be used over and over again and yet provide many different types of floss. For example, a user may be using waxed floss, and may wish to change to unwaxed floss, or flavored floss such as mint flavored floss, dental tape, shred resistent floss, or the like. If the user owns one of the present dispensers, he or she can simply remove the container in the support member and replace it with a new container containing the particular type of floss which the user wishes to switch to. In fact, in preferred embodiments of the present invention, the support member is designed to accommodate more than one floss container so that a user or a family of users may select between more than one kind of floss which is available from the same dispenser. Alternate embodiments are combined with room fixtures such as a brush holder, soap dish, night light or the like which may provide for convenient use of space and/or marketability.

In addition to the convenience provided by the ability to dispense many different types of floss from the present floss dispenser at different times, or preferably at the same time, convenience is also provided by locating the floss in a readily accessible location for use. The floss dispenser of the present invention can be wall mounted in the bathroom or can be structured to stand on a shelf or any other flat surface. Instead of being inside a drawer, or a medicine cabinet, the floss can be located in a location chosen for its enhanced visibility in order to provide a convenient reminder to the user or users to make use of the floss and, thereby, improve their personal hygiene habits and the health of their teeth and gums at the same time.

It will be appreciated that the floss cassette or container can be easily mass produced to lower the unit cost of each container. It will preferably be made of a synthetic polymer material which is suitable for use in injection molding manufacturing processes. Since the container has no working parts and the materials needed to make the parts can be relatively inexpensive, it will be relatively economical. It will, therefore, provide for a clean, efficacious, economical, and convenient system for providing dental floss to users.

These and various other advantages and features of novelty which characterize the present invention are pointed out with particularity in the claims annexed hereto and forming a part hereof. However, for a better understanding of the present invention, its advantages, and any other objects obtained by its use, reference should be made to the drawings which form a further part hereof and to the accompanying descriptive matter, in which there is illustrated and described preferred embodiments of the present invention.

BRIEF DESCRIPTION OF THE DRAWINGS

In the drawings, in which like reference numerals indicate corresponding parts of preferred embodiments of the present invention throughout the several views.

FIG. 8 is a perspective view of a second alternate floss dispenser including a second alternate floss container in accordance with the present invention;

FIG. 9 is an enlarged perspective view of the alternate floss dispenser shown in FIG. 8;

FIG. 10 is an expanded sectional view of the alternate floss dispenser shown in FIG. 9 as seen from the line 10—10 thereof;

FIG. 11 is an expanded sectional view of a part of the dispenser shown in FIG. 10; and FIG. 12 is a perspective view of a third alternate floss dispenser in accordance with the present invention.

DETAILED DESCRIPTION OF THE PREFERRED EMBODIMENTS

Figure 1:
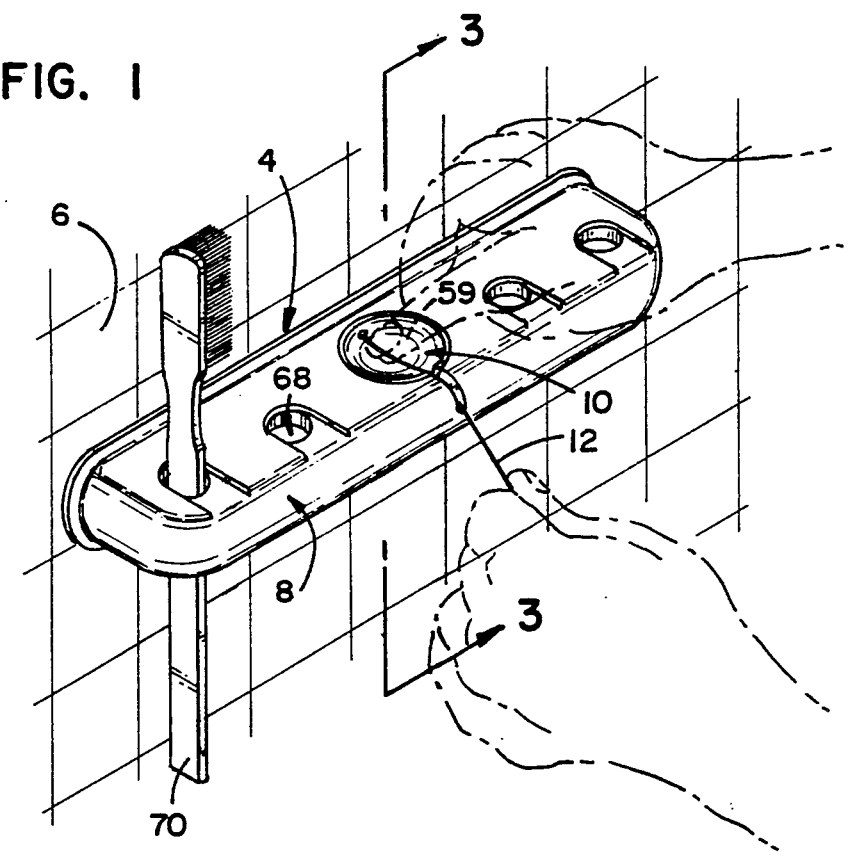
FIG. 1 is a perspective view of a floss dispenser in accordance with the present invention, including a floss container.
Figure 2:
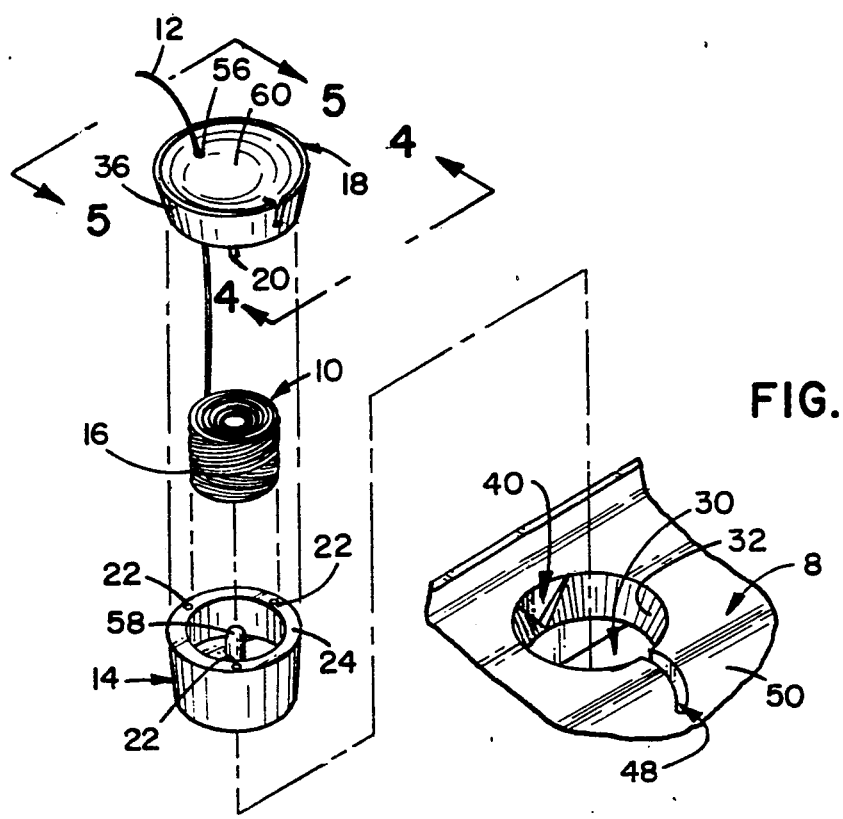
FIG. 2 is an exploded perspective view of the floss container shown in FIG. 1.

Referring now to the drawings, and to FIGS. 1-2 in particular, a dental floss dispenser 4 for attachment preferably to a substantially flat surface 6 is shown. The dispenser 4 includes a support member 8 for attachment to the surface 6 and a self-contained disposable cassette housing mechanism 10 or dental floss container 10 for storage of dental floss 12 or the like. As shown in the exploded perspective view shown in FIG. 2, the dental floss container 10 includes a housing made up of a receptacle 14 for receiving gathered dental floss, preferably a spool 16, and a cap 18 having pins 20 which are designed to fit into pin receiving openings 22 on an upper edge 24 of the receptacle 14. The cap 18 and the receptacle 14 are designed so that they remain together as a single two-piece unit or housing 11 once the receptacle 14 has received a spool 16 of dental floss 12 during manufacture or assembly, and the cap 18 has been placed on the receptacle 14. The fit between the pins 20 and the pin receiving openings 22 is an interference fit which makes it difficult to remove the cap 18 from the receptacle 14 once it is placed on the receptacle 14. One can remove the cap 18 from the receptacle 14, however, if one exerts sufficient force to pull the pins 20 out of the pin receiving openings 22 which provide a measurable resistance to the removal of the pins 20 therefrom. It will be appreciated, however, that any other known securing methods can be used in alternate embodiments of the present invention to secure the cap 18 to the receptacle 14. Such methods include the construction of a male-female joint having an interference fit to join the cap 18 to the receptacle 14, providing a pressure sensitive adhesive material to seal the joint therebetween, or the like.

The support member 8 includes a floss container receiving opening 30 whose inner wall 32 is designed to receive and support the container 10. The inner wall 32 of the opening 30 is slightly beveled so that the inner wall 32 specifically supports an angled outer edge 36 of the cap 18. A wedge-shaped slot 40 in the inner wall 32 is designed to receive and reciprocate a roughly triangular protrusion 42 on a back side of the cap 18 as shown in FIG. 5. The slot 40 and the triangular protrusion 42 must be in general alignment in order to allow the container 10 to fit properly into the floss container receiving opening 30. When the slot 40 and the protrusion 42 are in proper alignment and the container 10 is properly seated in the floss container receiving opening 30 a cap channel 46 in the cap 18 is aligned with a support member channel 48 in a front edge 50 of the support member 8 to facilitate the withdrawal of dental floss 12 from the container 10. The support member 8 also includes a pressure sensitive adhesive backing 54 (not shown, see FIG. 3) which allows one to easily attach the support member 8 to a substantially flat surface 6 such or a bathroom wall 6 by pressing the backing 51 against the surface 6. It will be appreciated, however, that any other known attachment methods can be used to attach alternate embodiments of the present invention to respective surfaces. The support member 8 is also includes a plurality of toothbrush receiving openings 68, designed to receive and retain a toothbrush 70.

Figure 3:
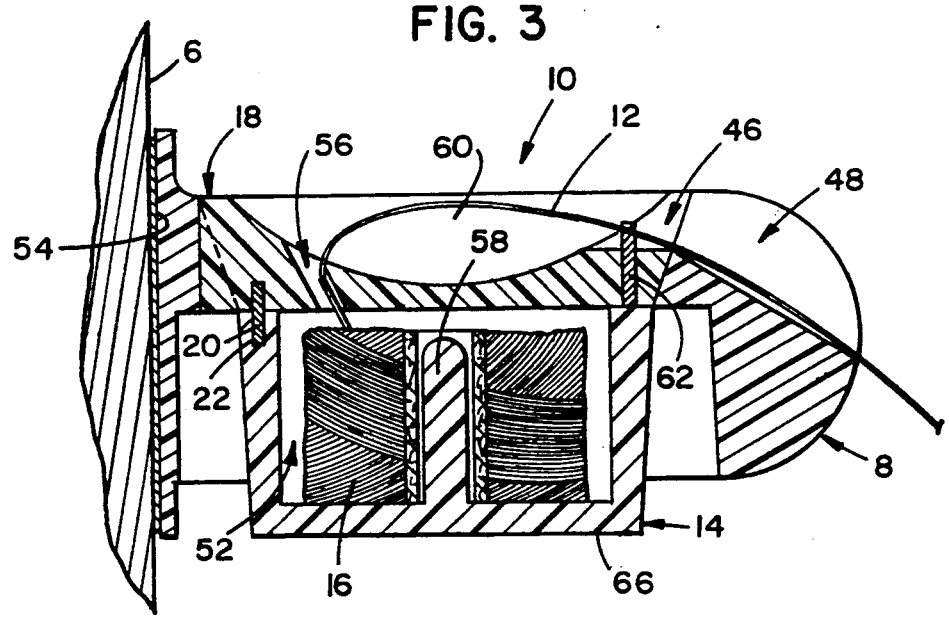
FIG. 3 is a sectional view of the floss dispenser of the present invention shown in FIG. 1 as seen generally from the line 3—3.
Figures 4, 5:
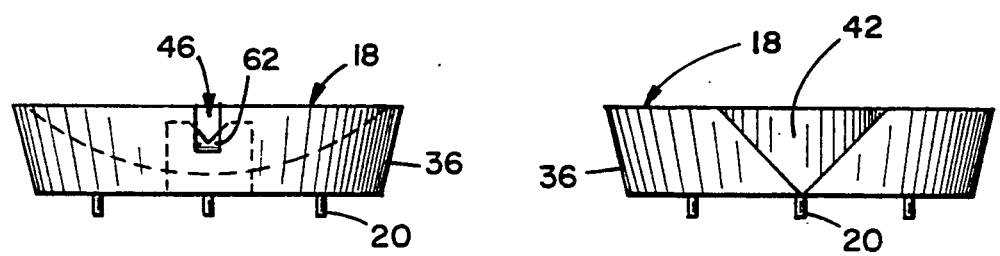
FIG. 4 is a side view of a cap of the container as seen from the line 4—4 of FIG. 2.
FIG. 5 is a side view of the cap as seen from the line 5—5 of FIG. 2.
Figure 6:
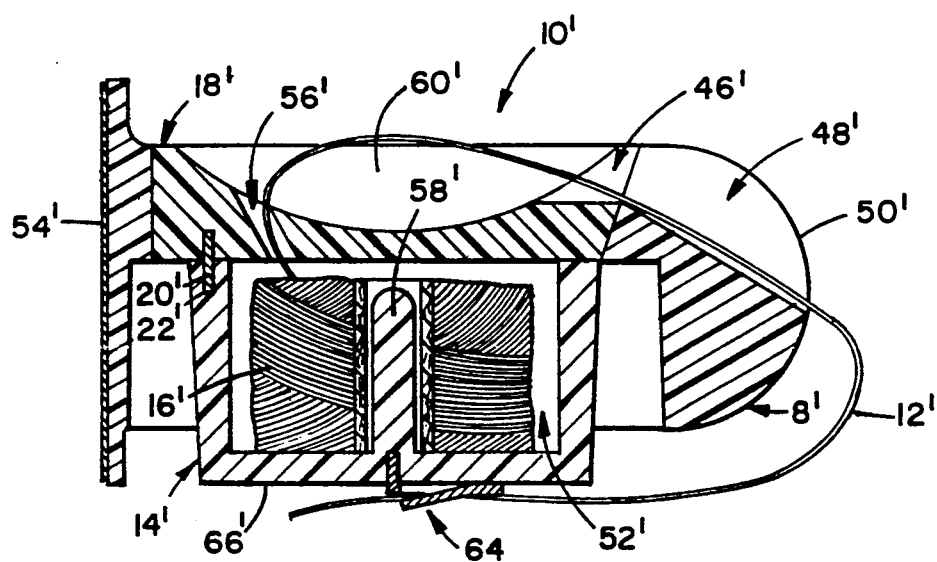
FIG. 6 is a sectional view similar to that shown in FIG. 3 of an alternate floss dispenser including an alternate floss container.

Referring now also to FIGS. 3, 4 and 5, the dental floss 12 is removed from an enclosure 52 within the housing 11 created by the union of the receptacle 14 and the cap 18, by drawing the dental floss 12 through a narrow floss dispensing opening 56 in the cap 18. The floss dispensing opening is preferably oriented at angle which accommodates the removal of floss 12 from the spool 16 so that the floss 12 can come away from the side of the spool 16 as the spool 16 rotates about the floss receiving post 58 and pass substantial straight into the floss dispensing opening 56. In addition, the floss dispensing opening 56 is preferably large enough to allow floss 12 to pass therethrough freely and small enough to resist the passage of a drop of liquid. The dispensing opening preferably has a cross-sectional diameter of about 0.5–2.0 mm.

During assembly of the container 10, the floss 12 is preferably drawn through a floss dispensing opening 56 after the spool 16 is placed in the receptacle 14 on the floss receiving post 58 which the spool 16 can rotate about as the floss 12 is withdrawn. The floss 12 is drawn through the floss dispensing opening 56 before the cap 18 is attached or joined to the receptacle 14 to create the enclosure 52 within the single two-piece housing 11 create thereby.

In the preferred embodiment shown in FIGS. 1–4, the floss 12 is cut after it is withdrawn from the floss container 10 via the floss dispensing opening 56, by placing a finger 59 on the floss 12 and securing the floss 12 against an upper surface 60 of the cap 18 and pulling the floss 12 across a knife blade 62 in the cap channel 46 which cuts the floss 12, as is shown in FIG. 1. The upper surface 62 is preferably an indented or concave surface designed for this purpose.

In an alternate embodiment of the dental floss container 10' shown in FIG. 5, a floss clip 64 is attached to the bottom surface 66' of the alternate receptacle 14'. When an individual is using the alternate embodiment, the floss 12' is drawn out of the container 10' via the floss dispensing opening 56' and drawn over the front edge 50' of the support member 8' via the cap channel 46' and the support channel 48', and then under the support member 8' where it can be looped around the floss clip 64 and then pulled into the floss clip 64 where it is cut. It will be appreciated that the mechanism for cutting the floss 12' which is attached to the bottom surface 66' of the floss container 10' may be any known cutting mechanism, preferably a cutting mechanism known for cutting dental floss 12. Furthermore, the floss clip 64 of the present invention is a floss clip which is very well known in the art and is exemplified by the cutting mechanisms used by Castelli et al. (U.S. Pat. No. 2,929,541).

Figure 7:
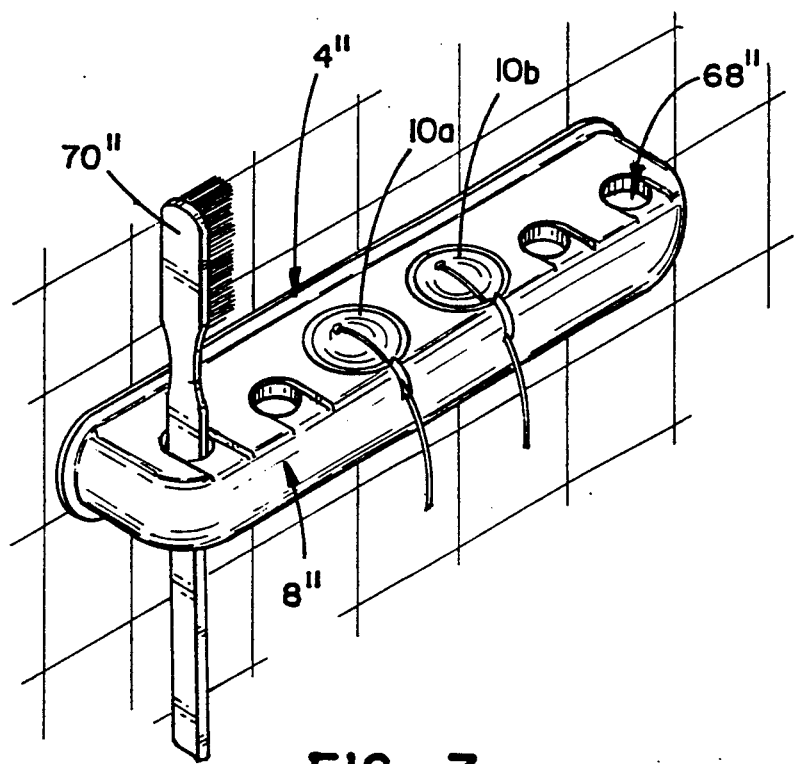
FIG. 7 is perspective view of an alternate embodiment of the floss dispenser of the present invention.

In FIG. 7, an alternate embodiment of the floss dispenser 4" is shown which includes a plurality of floss containers 10a and 10b which are received in a support member 8". This alternate embodiment has all of the respective features of the embodiment shown in FIGS. 1–4. It will be appreciated, however, that there are other embodiments having other features within the scope of the present invention as herein set forth.

Referring to FIGS. 8–11, yet another alternate embodiment of the dental floss dispenser 4''' is now disclosed as follows. The floss dispenser 4''' shown in FIGS. 8–11 is an object which can rest on a surface 72. This dispenser 4''' is preferably a paper weight or the like which may be placed upon any surface 72 including but not limited to a table (as shown) 72, a desk, a bookshelf, the dash of an automobile, or the like. An object of this particular embodiment is to provide a dispenser 4''' which is an item of artistic beauty; item having significant luxury value, physical beauty, attractiveness or the like such that it will be retained in convenient places for providing dental floss 12''' for the user. It will be appreciated that the dispenser 4''' need not be expensive. However, it is believed that if such a dispenser 4''' were expensive, particularly if it also had significant physical beauty or attractiveness so that it would be considered a luxury item, the novelty of such an item could be employed to market dental floss as well as to promote the frequent use of dental floss to floss one's teeth. Insofar as the demographics of the world's population, particularly the population in western countries such as the United States and the like, is an aging population, and insofar as a significant segment of this population possesses adequate expendable funds to easily afford small luxury items to employ as paper weights and the like, it is believed that a dispenser 4''' of this type may be an effective way to promote the use of dental floss.

The dental floss dispenser 4''' shown in FIGS. 8–10 has many of the features of the aforementioned embodiments of the present invention. It includes a support member 8'''' having a floss container 10''' or self-contained disposable cassette housing mechanism 10''' for storage of dental floss 12''' or the like. The cassette housing mechanism 10''' or floss container 10''' is received in a floss container receiving opening 30''' having an inner wall 32''' including a generally planar recess 34 extending around the floss container receiving opening 30''' on the inner wall 32''' of the support member 8'''' generally in a single plane, preferably in a generally horizontal plane, when the support member 8'''' is resting on a flat horizontal surface. The alternate floss container 10''' can be easily removed from and easily inserted into the floss container receiving opening 30''' of the alternate support member 8'''. The alternate floss container 10''' or parts used to make the floss container 10''' are preferably made of a suitable polymeric material which is preferably made by a molding or a pressing operation. The preferred alternate floss container 10''' is a self-contained unit made by joining an upper portion 18''' to a lower portion 14''', wherein the dental floss 12''' is gathered around a center portion 58a''' of the lower portion 14''' prior to joining the two parts together. The center portion 58a''' of the lower portion 14''' is preferably fused or otherwise bonded or affixed to a center portion 58b''' of the upper portion 18'''. A sealed or fused joint 35 also exists between the upper and lower lip portions 37b and 37a of the upper and lower portions 18''' and 14''' which join to form a lip 26 of an outer edge 27 of the container 10'''.

The floss container 10''' is preferably somewhat flexible. In preferred embodiments this container 10''' is sufficiently flexible to allow it to snap into place within the floss container receiving opening 30''' of the alternate support member 8'''. The floss container 10''' preferably includes the lip 26 which will snap into the generally planar recess 34 in the inner wall 32''' of the floss container receiver opening 30'''. The fit between the alternate floss container 10''' and the floss container receiving opening 30''' is preferably an interference fit which is preferably permitted because of the flexibility of the outer edge 27 of the alternate floss container 10''' including the lip 26, which is formed by joining the upper and lower lip portions 37b and 37a of the upper and lower portions 18''' and 14''' together.

The dental floss 12''' is withdrawn from the self-contained floss cassette housing mechanism 10''' by drawing it out of a small floss dispensing opening 56'''. The dental floss 12''' will rotate around the respective center portions 58a''' and 58b''' as the dental floss 12''' is withdrawn from the dispensing opening 56'''. When the dental floss 12''' has been withdrawn to a sufficient length for the intended use, it can be cut by drawing it over an alternate knife blade 63, similar to the knife blade 62 described herein above, but embedded in the support member 8'''.

When the dental floss 12''' contained in the floss cassette housing mechanism 10''' or container 10''' is used up and the container 10''' is empty, the floss container 10''' will be replaced with another floss container 10''' that contains a new or unused supply of dental floss 12'''. It is envisioned that one would be able to buy a box of floss containers 10''' from one's dentist, a drug store or the like, or one could buy individual floss containers 10''' from any of these sources when they are needed. The floss container 10''' is preferably individually wrapped (not shown) in a sealed envelope (not shown) or the like in order to ensure the cleanliness of the dental floss 12''' prior to use thereof. The envelope (not shown) can be opened, and the floss container 10''' contained therein can then be inserted into the floss container receiving opening 30''', once the empty floss container 10''' has been removed therefrom. The empty floss container 10''' can be removed by inserting a pointed object such as an end of a paper clip (not shown) or the like, which can be inserted into the floss dispensing opening 56''' in order to obtain a sufficient grip to pull the empty floss container 10''' out of the floss container receiving opening 30'''. Once the empty floss container 10''' is removed from the receiving opening 30''', the new floss container 10''' can be inserted therein.

Referring now also to FIG. 12, the alternate floss container 10''' of the present invention which is described herein above, can also be inserted into a floss container receiving opening 30'''' virtually identical to the shape and configuration of the floss container receiving opening 30''' described herein above, but located in a support member 8'''' which is preferably a common item which one would otherwise carry in a pocket or a personal carrying device such as an attach kit, a purse or the like. The dental floss dispenser 4'''' shown in FIG. 10 is a compact 4'''' which is generally carried in a purse or a toiletries bag for convenient personal use by the owner. It will be appreciated that it can also be carried in a pocket or any other place where similar small personal items are carried.

The compact floss dispenser 4'''' includes a floss container 10''' which is identical to the floss container shown in FIG. 10. The floss container 10''' shown in FIG. 11 is shown in position within the floss container receiver opening 30'''' of the upper section 80 of the compact floss container 4''''. The floss container 10''' can be removed from and inserted into the receiving opening 30'''' with relative ease. When all of the floss 12''' has been withdrawn from the container 10''', it is popped out of the floss container receiving opening 30'''' by placing a pointed object in the floss dispensing opening 56''' and popping or prying the floss container 10''' easily out of the floss container receiving opening 30''''. The floss container receiving opening 30'''' is then free to receive a new floss container 10''' which will be a renewable item which will preferably be available at local department stores, drug stores, and the like, or at one's dentist office. In this way, one may retain the pocket object 4'''' of the present invention over a period of time which extends beyond the supply lifetime of the dental floss 12''' contained in a single floss container 10'''. When the supply of dental floss 12''' in the floss container 10''' runs out, the empty floss container 10''' may be removed from the support member 8'''' of the pocket object 4'''' and a new floss container 10''', containing a new supply of dental floss 12''', can be inserted into the receiving opening 30'''' to replace the now emptied or used floss container 10''' which has been removed.

The preferred compact dental floss dispenser 4'''' includes a lower section 82 which is pivotally attached to the upper section 80 by a hinge (not shown) which enables the compact floss dispenser 4'''' to be opened so that one can have access either to floss 12''' or the rouge 84 located in the lower section. The upper section 80 also includes a mirror 86. Interposed between the upper section 80 and the lower section 82 is a cover section 88 which is pivotally attached to the lower section to proximate the hinge (not shown). The cover section 88 separates the rouge 84 so that the amount of rouge which would otherwise collect upon the floss container 10''' can be minimized, or preferably eliminated.

It is to be understood, however, that even though numerous characteristics and advantages of the present invention have been set forth in the foregoing description, together with details of the structure and function of the invention, the disclosure is illustrative, and changes in matters of order, shape, size and arrangement of parts may be made within the principles of the invention and to the full extent indicated by the broad general meaning of the terms in which the appended claims are expressed.

What is claimed is:

1. A dental floss container for storage of dental floss, said container for engagement with a support member, the support member having means for supporting said container, said container comprising:
   a) a housing, said housing including an enclosure for substantially cleanly storage of the dental floss prior to being dispensed, said housing including introduction means for introducing dental floss into said enclosure, said housing including a floss dispensing opening through which the floss can be passed and withdrawn; wherein said housing includes a receptacle and cap means for covering said receptacle, said receptacle has interior and exterior walls and said cap means has inside and outside surfaces; and wherein said inside surface and said interior wall define said enclosure when said cap means is engaged with said receptacle; wherein said housing includes cutting means for cutting the floss after it is withdrawn from said container; and wherein said cap means includes a cap having a plurality of pins, said receptacle including a plurality of pin receiving openings which receive said pins when the cap is joined with the receptacle to form a single two-piece housing unit.

2. The dental floss container of claim 1 wherein said housing includes upper and lower portions, orientation means for orienting said housing with respect to the support member, and engaging means for engaging said housing with the support member.

3. The dental floss container of claim 1 wherein said receptacle includes a floss receiving post about which dental floss gathered in a spool can rotate.

4. The dental floss container of claim 1 wherein said cutting means is a knife blade incorporated into said cap such that dental floss withdrawn from a floss dispensing opening in said cap can be drawn across said knife blade to cut the floss.

5. The dental floss container of claim 1 wherein said cutting means includes a floss cutting clip attached to said receptacle.

6. A dental floss dispenser, comprising:
a) self-contained disposable cassette housing means for enclosing dental floss gathered for storage therein prior to being dispensed, said disposable cassette housing means including a gathered supply of dental floss; and
b) support means for supporting said disposable cassette housing means, said support means having a front and a cassette housing receiving means comprising a receiving opening for receiving and supporting said disposable cassette housing means wherein one of said disposable cassette housing means and said cassette housing receiving means includes an orienting protrusion and the other of said disposable cassette housing means and said cassette housing receiving means includes a protrusion receiving orienting slot, wherein said orienting protrusion and said orienting slot cooperate to align said disposable cassette housing means in respect to said front when said disposable cassette housing means is received in said receiving opening.

7. The dental floss dispenser of claim 6 wherein said disposable cassette housing means includes a single two-piece housing including an upper portion and a lower portion which are joined together to create an enclosure therein for said gathered supply of dental floss, said upper portion including a floss dispensing opening from which a strand of the gathered dental floss may be withdrawn and dispensed.

8. The dental floss dispenser of claim 7 wherein said upper portion includes the orienting protrusion and said receiving opening includes the protrusion receiving orienting slot, wherein said protrusion and said slot are adapted to align said housing with said support means.

9. The dental floss dispenser of claim 8 wherein said upper portion includes a floss dispensing opening and a knife-blade, said knife blade being incorporated in a cap channel, said support means including a support channel, wherein said cap channel and said support channel are in alignment when said housing are aligned in said support means by the cooperative of said protrusion and said slot, said knife blade including a cutting edge for cutting the dental floss after it is withdrawn from said housing.

10. The dental floss dispenser of claim 6 wherein said support means includes a pressure sensitive adhesive backing for attachment with a surface.

11. The dental floss dispenser of claim 10 wherein said support means includes a plurality of tooth-brush receiving openings.

12. The dental floss dispenser of claim 10 wherein said support means includes a plurality of of said receiving openings and wherein said disposable cassette housing means include a plurality of single two-piece floss containers, each floss container including a cap and a receptacle which enclose a spool of dental floss contained therein and means for withdrawing a single strand of dental floss from said spool of floss enclosed within said container.

13. A dental floss dispenser for resting on a surface, said dental floss dispenser comprising:
(a) self-containing disposable cassette housing means for enclosing dental floss gathered for storage therein prior to being dispensed, said disposable cassette housing means including; and
(b) a support member for retention of the dispenser on the surface, said support member including support means for supporting said disposable cassette housing means, said support member including a receiving opening which receives said disposable cassette housing means, wherein one of said disposable cassette housing means and said receiving opening includes an orienting protrusion and the other of said disposable cassette housing means and said receiving opening includes a protrusion receiving orienting slot, and wherein said orienting protrusion and said orienting slot cooperate to align said disposable cassette housing means in respect to a front of said support member when said disposable cassette housing means is received in said receiving opening.

14. A dental floss dispenser kit, comprising:
(a) a self-contained disposable cassette housing means for enclosing dental floss gathered for storage therein prior to being dispensed, said disposable cassette housing means including (i) a gathered supply of dental floss, and (ii) means for withdrawing the dental floss from within said housing means; and
(b) support means for receiving and supporting said disposable cassette housing means, said support means including a support member having receiving means with a receiving opening for detachably receiving and supporting said disposable housing means, wherein said disposable cassette housing means are removable from said receiving means so as to be replaceable, wherein one of said disposable cassette housing means and said receiving means includes an orienting protrusion and the other of said disposable cassette housing means and said receiving means includes a protrusion receiving orienting slot, wherein said orienting protrusion and said orienting slot are adapted to align said disposable cassette housing means in respect to a front of said support means when said receiving opening receives said disposable cassette housing means.

15. The dental floss dispenser kit of claim 14, wherein said self-contained disposable cassette housing means include a self-contained disposable dental floss cassette including a gathered supply of dental floss for cleanly storage therein and for being dispensed therefrom, and a dental floss withdrawing opening in a surface of the cassette, wherein the dental floss can be withdrawn from the cassette via the withdrawing opening.

16. A dental floss dispenser kit of claim 15, wherein said receiving opening which receives and supports said disposable dental floss cassette and said receiving opening being configured and sized to provide for an interference fit between the cassette and said receiving opening, wherein said cassette can be easily removed from or inserted into said receiving opening so as to be removable and replaceable.

* * * * *